(12) United States Patent
Liao et al.

(10) Patent No.: US 8,204,599 B2
(45) Date of Patent: Jun. 19, 2012

(54) SYSTEM FOR ANCHORING AN IMPLANTABLE SENSOR IN A VESSEL

(75) Inventors: Wangcai Liao, Cary, NC (US); Bin Mi, Plymouth, MN (US); Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1074 days.

(21) Appl. No.: 12/103,963

(22) Filed: Apr. 16, 2008

(65) Prior Publication Data
US 2008/0275350 A1 Nov. 6, 2008

Related U.S. Application Data

(60) Provisional application No. 60/915,567, filed on May 2, 2007.

(51) Int. Cl.
*A61N 1/00* (2006.01)
(52) U.S. Cl. .......................................................... 607/44
(58) Field of Classification Search ........................ None
See application file for complete search history.

(56) References Cited

U.S. PATENT DOCUMENTS

| | | | |
|---|---|---|---|
| 3,874,388 A | 4/1975 | King et al. |
| 4,391,124 A | 7/1983 | Drost et al. |
| 4,407,296 A | 10/1983 | Anderson |
| 4,485,813 A | 12/1984 | Anderson et al. |
| 4,492,107 A | 1/1985 | Sandhu |
| 4,672,976 A | 6/1987 | Kroll |
| 4,836,204 A | 6/1989 | Landymore et al. |
| 4,846,191 A | 7/1989 | Brockway et al. |
| 4,900,303 A | 2/1990 | Lemelson |
| 4,917,089 A | 4/1990 | Sideris |
| 4,966,148 A | 10/1990 | Millar |
| 5,040,538 A | 8/1991 | Mortazavi |
| 5,218,965 A | 6/1993 | Ring |
| 5,284,138 A | 2/1994 | Kujawski |
| 5,303,207 A | 4/1994 | Brady et al. |
| 5,334,217 A | 8/1994 | Das |
| 5,411,551 A | 5/1995 | Winston et al. |
| 5,415,630 A | 5/1995 | Gory et al. |

(Continued)

FOREIGN PATENT DOCUMENTS
EP 0897690 2/1999
(Continued)

OTHER PUBLICATIONS

Goodall, Eleanor V. et al., "Position-Seletive Activation of Peripheral Nerve Fibers with a Cuff Electrode", IEEE Transactions on Biomedical Engineering, IEEE Service Center, Piscataway, NJ, US, vol. 43, No. 8, Aug. 1, 1996.

(Continued)

*Primary Examiner* — Shafiqul Haq
(74) *Attorney, Agent, or Firm* — Faegre Baker Daniels LLP

(57) ABSTRACT

A system and a method of disposing a second sensor module overlying a first sensor module system is described. A first assembly including an expandable anchor and a sensor module is at least partially overlapped by a second assembly including an expandable anchor and a sensor module. If necessary or desired, the functions of the second sensor module can replace the functions of the first sensor module. The sensor module may include a blood pressure sensor.

10 Claims, 6 Drawing Sheets

U.S. PATENT DOCUMENTS

| | | | |
|---|---|---|---|
| 5,451,235 | A | 9/1995 | Lock et al. |
| 5,604,531 | A | 2/1997 | Iddan et al. |
| 5,634,936 | A | 6/1997 | Linden et al. |
| 5,656,036 | A | 8/1997 | Palmaz |
| 5,662,711 | A | 9/1997 | Douglas |
| 5,704,352 | A | 1/1998 | Tremblay et al. |
| 5,725,552 | A | 3/1998 | Kotula et al. |
| 5,733,313 | A | 3/1998 | Barreras, Sr. et al. |
| 5,772,669 | A | 6/1998 | Vrba |
| 5,775,331 | A | 7/1998 | Raymond et al. |
| 5,800,497 | A | 9/1998 | Bakels et al. |
| 5,824,053 | A | 10/1998 | Khosravi et al. |
| 5,833,603 | A | 11/1998 | Kovacs et al. |
| 5,855,563 | A | 1/1999 | Kaplan et al. |
| 5,860,923 | A | 1/1999 | Lenker et al. |
| 5,891,154 | A | 4/1999 | Loeffler |
| 5,967,980 | A | 10/1999 | Ferre et al. |
| 5,967,986 | A | 10/1999 | Cimochowski et al. |
| 5,967,989 | A | 10/1999 | Cimochowski et al. |
| 5,995,876 | A | 11/1999 | Kruse et al. |
| 6,002,969 | A | 12/1999 | Machek et al. |
| 6,015,386 | A | 1/2000 | Kensey et al. |
| 6,015,387 | A | 1/2000 | Schwartz et al. |
| 6,030,413 | A | 2/2000 | Lazarus |
| 6,033,366 | A | 3/2000 | Brockway et al. |
| 6,053,873 | A | 4/2000 | Govari et al. |
| 6,076,016 | A | 6/2000 | Feierbach |
| 6,097,984 | A | 8/2000 | Douglas |
| 6,106,464 | A | 8/2000 | Bass et al. |
| 6,140,740 | A | 10/2000 | Porat et al. |
| 6,159,156 | A | 12/2000 | Van Bockel |
| 6,179,858 | B1 | 1/2001 | Squire et al. |
| 6,193,745 | B1 | 2/2001 | Fogarty et al. |
| 6,214,025 | B1 | 4/2001 | Thistle et al. |
| 6,231,516 | B1 | 5/2001 | Keilman |
| 6,236,889 | B1 | 5/2001 | Soykan et al. |
| 6,239,724 | B1 | 5/2001 | Doron et al. |
| 6,240,312 | B1 | 5/2001 | Alfano et al. |
| 6,246,898 | B1 | 6/2001 | Vesely et al. |
| 6,277,078 | B1 | 8/2001 | Porat et al. |
| 6,278,790 | B1 | 8/2001 | Davis et al. |
| 6,309,350 | B1 | 10/2001 | Van Tassel |
| 6,328,699 | B1 | 12/2001 | Eigler et al. |
| 6,331,163 | B1 | 12/2001 | Kaplan |
| 6,379,308 | B1 | 4/2002 | Brockway et al. |
| 6,409,674 | B1 | 6/2002 | Brockway et al. |
| 6,416,474 | B1 | 7/2002 | Penner et al. |
| 6,432,050 | B1 | 8/2002 | Porat et al. |
| 6,442,413 | B1 | 8/2002 | Silver |
| 6,447,522 | B2 | 9/2002 | Gambale et al. |
| 6,475,170 | B1 | 11/2002 | Doron et al. |
| 6,486,588 | B2 | 11/2002 | Doron et al. |
| 6,527,780 | B1 | 3/2003 | Wallace et al. |
| 6,543,272 | B1 | 4/2003 | Vitek |
| 6,585,763 | B1 | 7/2003 | Keilman et al. |
| 6,592,553 | B2 | 7/2003 | Zhang et al. |
| 6,628,989 | B1 | 9/2003 | Penner et al. |
| 6,645,143 | B2 | 11/2003 | Van Tassel et al. |
| 6,660,021 | B1 | 12/2003 | Palmer et al. |
| 6,685,638 | B1 | 2/2004 | Taylor et al. |
| 6,699,186 | B1 | 3/2004 | Wolinsky et al. |
| 6,702,847 | B2 | 3/2004 | DiCarlo |
| 6,730,108 | B2 | 5/2004 | Van Tassel et al. |
| 6,738,671 | B2 | 5/2004 | Christophersom et al. |
| 6,743,173 | B2 | 6/2004 | Penner et al. |
| 6,746,404 | B2 | 6/2004 | Schwartz |
| 6,747,916 | B1 | 6/2004 | Fleury et al. |
| 6,755,855 | B2 | 6/2004 | Yurek et al. |
| 6,764,446 | B2 | 7/2004 | Wolinsky et al. |
| 6,783,499 | B2 | 8/2004 | Schwartz |
| 6,800,060 | B2 | 10/2004 | Marshall |
| 6,840,956 | B1 | 1/2005 | Wolinsky et al. |
| 6,855,115 | B2 | 2/2005 | Fonseca et al. |
| 6,868,288 | B2 | 3/2005 | Thompson |
| 6,890,303 | B2 | 5/2005 | Fitz |
| 6,899,729 | B1 | 5/2005 | Cox |
| 6,904,308 | B2 | 6/2005 | Frisch et al. |
| 6,920,347 | B2 | 7/2005 | Simon et al. |
| 6,926,670 | B2 | 8/2005 | Rich |
| 6,934,573 | B1 | 8/2005 | Glukhovsky et al. |
| 6,950,690 | B1 | 9/2005 | Meron et al. |
| 6,958,034 | B2 | 10/2005 | Iddan |
| 6,970,742 | B2 | 11/2005 | Mann et al. |
| 6,972,017 | B2 | 12/2005 | Smith et al. |
| 6,984,205 | B2 | 1/2006 | Gazdzinski |
| 7,001,329 | B2 | 2/2006 | Kobayashi et al. |
| 7,006,858 | B2 | 2/2006 | Silver et al. |
| 7,009,634 | B2 | 3/2006 | Iddan et al. |
| 7,011,671 | B2 | 3/2006 | Welch |
| 7,024,248 | B2 | 4/2006 | Penner et al. |
| 7,033,322 | B2 | 4/2006 | Silver |
| 7,035,684 | B2 | 4/2006 | Lee |
| 7,039,453 | B2 | 5/2006 | Mullick et al. |
| 7,060,038 | B2 | 6/2006 | Letort et al. |
| 7,064,472 | B2 | 6/2006 | Pelrine et al. |
| 7,065,409 | B2 | 6/2006 | Mazar |
| 7,076,305 | B2 | 7/2006 | Imran et al. |
| 7,083,822 | B2 | 8/2006 | Brightbill |
| 7,116,352 | B2 | 10/2006 | Yaron |
| 7,118,529 | B2 | 10/2006 | Glukhovsky et al. |
| 7,118,531 | B2 | 10/2006 | Krill |
| 7,131,986 | B2 | 11/2006 | Sirhan et al. |
| 7,160,258 | B2 | 1/2007 | Imran et al. |
| 7,198,603 | B2 | 4/2007 | Penner et al. |
| 7,211,045 | B2 | 5/2007 | Dala-Krish et al. |
| 7,273,457 | B2 | 9/2007 | Penner |
| 7,283,874 | B2 | 10/2007 | Penner |
| 7,308,319 | B2 | 12/2007 | Lovett et al. |
| 7,338,512 | B2 | 3/2008 | McGuckin, Jr. et al. |
| 7,347,868 | B2 | 3/2008 | Burnett et al. |
| 7,392,094 | B2 | 6/2008 | Zhang et al. |
| 7,437,193 | B2 | 10/2008 | Parramon et al. |
| 7,452,334 | B2 | 11/2008 | Gianchandani et al. |
| 7,477,946 | B2 | 1/2009 | Tockman et al. |
| 7,555,351 | B2 | 6/2009 | Zhang et al. |
| 7,744,542 | B2 * | 6/2010 | Piaget et al. .................. 600/529 |
| 7,780,694 | B2 | 8/2010 | Palmer et al. |
| 7,850,708 | B2 | 12/2010 | Pal |
| 7,890,188 | B2 | 2/2011 | Zhang et al. |
| 2002/0045920 | A1 | 4/2002 | Thompson |
| 2002/0123672 | A1 | 9/2002 | Christophersom et al. |
| 2002/0165601 | A1 | 11/2002 | Clerc |
| 2002/0183628 | A1 | 12/2002 | Reich et al. |
| 2002/0188207 | A1 | 12/2002 | Richter |
| 2003/0114897 | A1 | 6/2003 | Von Arx et al. |
| 2003/0139796 | A1 | 7/2003 | Sequin et al. |
| 2003/0200031 | A1 | 10/2003 | de Kok |
| 2004/0006377 | A1 | 1/2004 | Behm |
| 2004/0116992 | A1 | 6/2004 | Wardle et al. |
| 2004/0147969 | A1 | 7/2004 | Mann et al. |
| 2004/0176672 | A1 | 9/2004 | Silver et al. |
| 2004/0204744 | A1 | 10/2004 | Penner et al. |
| 2004/0215228 | A1 | 10/2004 | Simpson et al. |
| 2005/0080472 | A1 | 4/2005 | Atkinson et al. |
| 2005/0115561 | A1 | 6/2005 | Stahmann et al. |
| 2005/0124875 | A1 | 6/2005 | Kawano et al. |
| 2005/0136385 | A1 | 6/2005 | Mann et al. |
| 2005/0149108 | A1 | 7/2005 | Cox |
| 2005/0149128 | A1 | 7/2005 | Heil, Jr. et al. |
| 2005/0149155 | A1 | 7/2005 | Scheiner et al. |
| 2005/0149156 | A1 | 7/2005 | Libbus et al. |
| 2005/0154321 | A1 | 7/2005 | Wolinsky et al. |
| 2005/0165456 | A1 | 7/2005 | Mann et al. |
| 2005/0209678 | A1 | 9/2005 | Henkes et al. |
| 2005/0245840 | A1 | 11/2005 | Christopherson et al. |
| 2006/0009818 | A1 | 1/2006 | Von Arx et al. |
| 2006/0047205 | A1 | 3/2006 | Ludomirsky et al. |
| 2006/0064133 | A1 | 3/2006 | Von Arx et al. |
| 2006/0064134 | A1 | 3/2006 | Mazar et al. |
| 2006/0064142 | A1 | 3/2006 | Chavan et al. |
| 2006/0064143 | A1 | 3/2006 | Von Arx et al. |
| 2006/0079740 | A1 | 4/2006 | Silver et al. |
| 2006/0089627 | A1 | 4/2006 | Burnett et al. |
| 2006/0089694 | A1 | 4/2006 | Zhang et al. |
| 2006/0122522 | A1 | 6/2006 | Chavan et al. |
| 2006/0136004 | A1 | 6/2006 | Cowan et al. |
| 2006/0142819 | A1 | 6/2006 | Penner et al. |

| | | | |
|---|---|---|---|
| 2006/0149329 A1 | 7/2006 | Penner | |
| 2006/0149330 A1 | 7/2006 | Mann et al. | |
| 2006/0178586 A1 | 8/2006 | Dobak, III | |
| 2006/0206153 A1 | 9/2006 | Libbus et al. | |
| 2006/0241735 A1 | 10/2006 | Tockman et al. | |
| 2006/0259085 A1 | 11/2006 | Zhang et al. | |
| 2006/0287700 A1 | 12/2006 | White et al. | |
| 2006/0293741 A1 | 12/2006 | Johnson et al. | |
| 2007/0049833 A1 | 3/2007 | Tearney et al. | |
| 2007/0129637 A1 | 6/2007 | Wolinsky et al. | |
| 2007/0156126 A1 | 7/2007 | Flaherty | |
| 2007/0156205 A1 | 7/2007 | Larson et al. | |
| 2007/0162090 A1 | 7/2007 | Penner | |
| 2007/0179583 A1 | 8/2007 | Goetzinger et al. | |
| 2007/0191904 A1 | 8/2007 | Libbus et al. | |
| 2007/0208390 A1 | 9/2007 | Von Arx et al. | |
| 2007/0250126 A1 | 10/2007 | Maile et al. | |
| 2007/0274565 A1 | 11/2007 | Penner | |
| 2007/0282413 A1 | 12/2007 | Tockman et al. | |
| 2007/0282415 A1 | 12/2007 | Tockman et al. | |
| 2008/0071178 A1 | 3/2008 | Greenland et al. | |
| 2008/0071248 A1 | 3/2008 | Delgado et al. | |
| 2008/0071339 A1 | 3/2008 | Stalker et al. | |
| 2008/0108904 A1 | 5/2008 | Heil | |
| 2008/0176271 A1 | 7/2008 | Silver et al. | |
| 2008/0283066 A1 | 11/2008 | Delgado et al. | |
| 2009/0054793 A1 | 2/2009 | Nunez et al. | |
| 2009/0171274 A1 | 7/2009 | Harlev et al. | |
| 2009/0270742 A1 | 10/2009 | Wolinsky et al. | |
| 2010/0016840 A1 | 1/2010 | Stahmann et al. | |
| 2010/0210923 A1 | 8/2010 | Li et al. | |

FOREIGN PATENT DOCUMENTS

| | | |
|---|---|---|
| EP | 0928598 | 8/2000 |
| EP | 1068836 | 1/2001 |
| EP | 1488735 | 6/2007 |
| GB | 2333044 | 7/1999 |
| JP | H(11)-089942 | 4/1999 |
| JP | 2000-507142 | 6/2000 |
| JP | 2001-061790 | 3/2001 |
| WO | WO 83/03348 | 10/1983 |
| WO | 9934731 | 7/1999 |
| WO | WO 00/16686 | 3/2000 |
| WO | WO00/59376 | 10/2000 |
| WO | WO 01/67989 | 9/2001 |
| WO | WO 01/87137 | 11/2001 |
| WO | WO 2004/024034 | 3/2004 |
| WO | WO 2005/067817 | 7/2005 |
| WO | WO 2006/062725 | 6/2006 |
| WO | WO 2007/057739 | 5/2007 |
| WO | WO 2007/082115 | 7/2007 |
| WO | 2008002654 | 1/2008 |
| WO | WO 2008/034077 | 3/2008 |
| WO | WO 2008/057720 | 5/2008 |
| WO | WO2008/060197 | 5/2008 |
| WO | WO2008/144191 | 11/2008 |
| WO | 2009006610 | 1/2009 |

OTHER PUBLICATIONS

International Search Report and Written Opinion issued in PCT/US2010/020756, mailed Sep. 27, 2010.

Invitation to Pay Fees and Partial Search Report issued in PCT/US2010/020756, mailed May 12, 2010.

Lanning & Shandas, "Development and validation of implantable sensors for monitoring function of prosthetic heart valves: in vitro studies" Medical & Biological Engineering & Computing, Jul. 2003, vol. 41, issue 4, pp. 416-424.

Holmes et al., "Sirolimus-Eluting Stents vs. Vascular Brachytherapy for In-Stent Restenosis Within Bare-Metal Stents," JAMA 295 (11): 1264-1273, Mar. 15, 2006.

Wenaweser et al., "Stent thrombosis following bare-metal stent implantation: success of emergency percutaneous coronary intervention and predictors of adverse outcome," European Heart Journal 26: 1180-1187, 2005.

Stone et al., "Paclitaxel-Eluting Stents vs. Vascular Brachytherapy for In-Stent Restenosis Within Bare-Metal Stents," JAMA 295(11): 1253-1263.

Sheth et al., "Subacute Thrombosis and Vascular Injury Resulting From Slotted-Tube Nitinol and Stainless Steel Stents in a Rabbit Carotid Artery Model," Circulation 94: 1733-1740.

International Search Report and Written Opinion from PCT/US2008/062229, mailed Jan. 5, 2009.

* cited by examiner

US 8,204,599 B2

SYSTEM FOR ANCHORING AN IMPLANTABLE SENSOR IN A VESSEL

BENEFIT CLAIM

This application claims the benefit under 35 U.S.C. §119 (e) of U.S. Provisional Patent Application No. 60/915,567, filed on May 2, 2007, entitled "SYSTEM FOR ANCHORING AN IMPLANTABLE SENSOR IN A VESSEL" which is herein incorporated by reference in its entirety.

TECHNICAL FIELD

The present invention relates to medical devices and methods for anchoring implantable medical devices in the body. In particular, the present invention relates to anchoring devices and methods for anchoring implantable physiologic sensors and other implantable medical devices within a patient's vasculature.

BACKGROUND

Medical devices that can be implanted within a patient's body for monitoring one or more physiological parameters and/or to provide therapeutic functions are known. For example, sensors or transducers can be placed in the body for monitoring a variety of properties, such as temperature, blood pressure, strain, fluid flow, chemical properties, electrical properties, magnetic properties, and the like. In addition, medical devices can be implanted that perform one or more therapeutic functions, such as drug delivery, cardiac pacing, defibrillation, electrical stimulation, and the like.

One parameter of particular interest is blood pressure. One or more implantable pressure sensing modules can be used in conjunction with cardiac rhythm management (CRM) devices to facilitate optimization of CRM device settings. In such systems, the pressure sensing module is delivered transvenously to a target vessel (e.g., the pulmonary artery), and anchored in the vessel using various fixation techniques. Accurate placement and secure fixation of the sensing module are important factors in accurately and reliably measuring the desired parameter. After a period of time, a new functional sensor module to be implanted in the same approximate location. Alternatively, the first sensor module may become dislodged from its original position at the target location within the pulmonary artery and require repositioning.

SUMMARY

The present invention, according to one embodiment, is a sensor module system configured to be delivered and secured at a location within a pulmonary artery, which includes a first assembly and a second assembly. The first assembly includes a first sensor module coupled to a first expandable anchor. The second assembly includes a second sensor module coupled to a second expandable anchor. Each of the expandable anchors are configured to transition between a collapsed configuration and an expanded configuration. The first assembly is configured such that the first expandable anchor at least partially overlaps the second expandable anchor such that the second sensor module is spaced apart from the first sensor module.

According to another embodiment of the present invention, a sensor module system configured to be delivered and secured at a target location within a pulmonary artery includes a first assembly and a second assembly. The first assembly includes a first sensor module coupled to a first expandable anchor. The second assembly includes a second sensor module coupled to a second expandable anchor. Each of the expandable anchors are configured to transition between a collapsed configuration and an expanded configuration. The first and second expandable anchors include a first alignment feature and a second alignment feature, respectively. The first alignment feature is configured to align with the second alignment feature such that the second anchor is at least partially overlapped by the first anchor.

According to another embodiment of the present invention, a method of overlapping a first assembly including a first expandable anchor coupled to a first sensor module with a second assembly including a second expandable anchor and a second sensor module includes: evaluating the first sensor module assembly at a target location within the pulmonary artery; delivering the second assembly to the target location within the pulmonary artery; and positioning the second assembly such that the first expandable anchor at least partially overlaps the second expandable anchor.

According to yet another embodiment of the present invention, a method of reinforcing a first assembly including a first sensor module coupled to a first expandable anchor a target location within a pulmonary artery includes: delivering a second assembly including a second expandable anchor to the target location within the pulmonary artery; overlapping a portion of the first assembly with a portion of the second assembly such that the first anchor at least partially overlaps the second anchor; and expanding the second expandable anchor such that a position of the first expandable anchor is reinforced at the target location.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
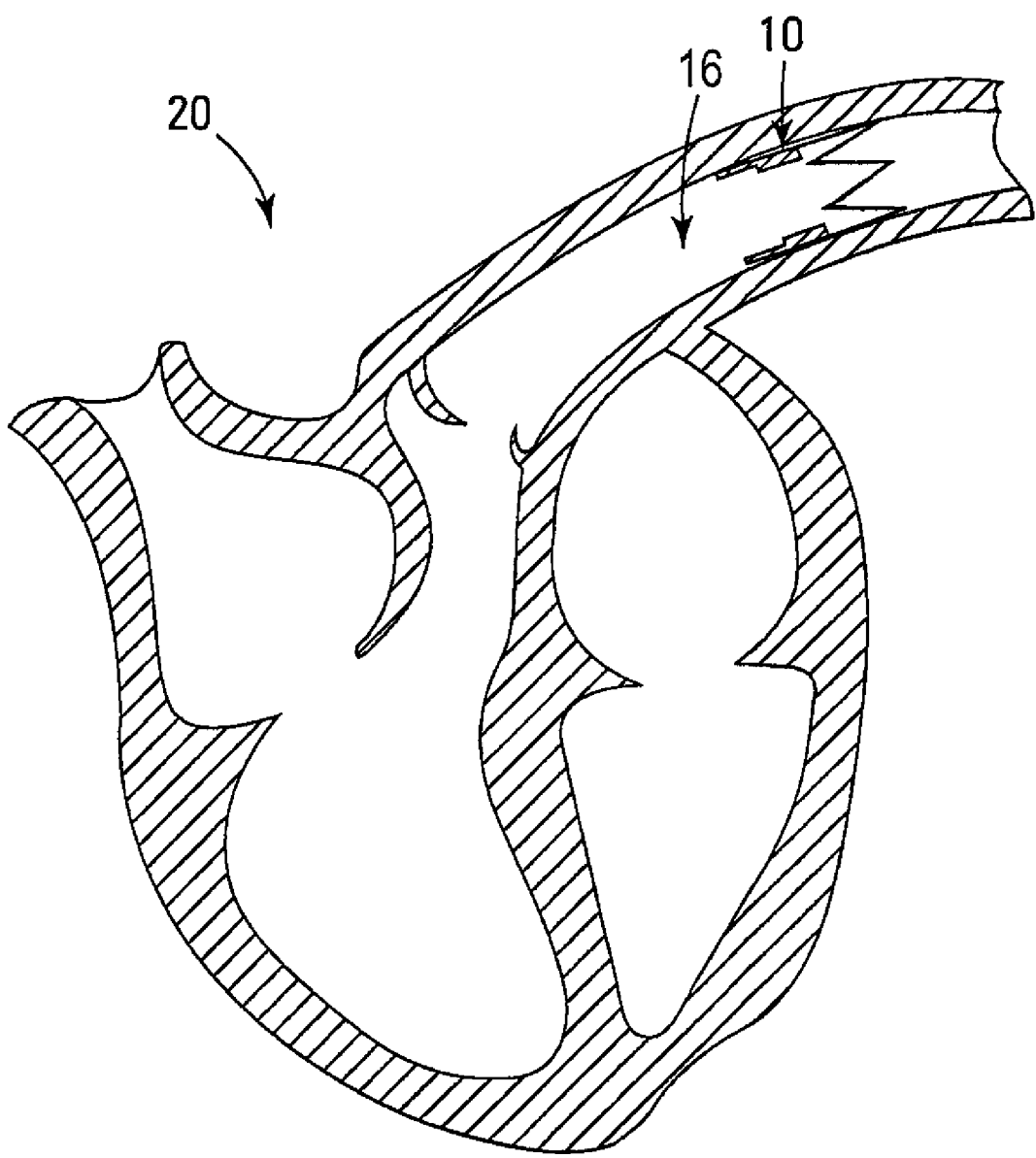
FIG. 1 is a schematic view of a sensor module system deployed at a location within the pulmonary artery according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
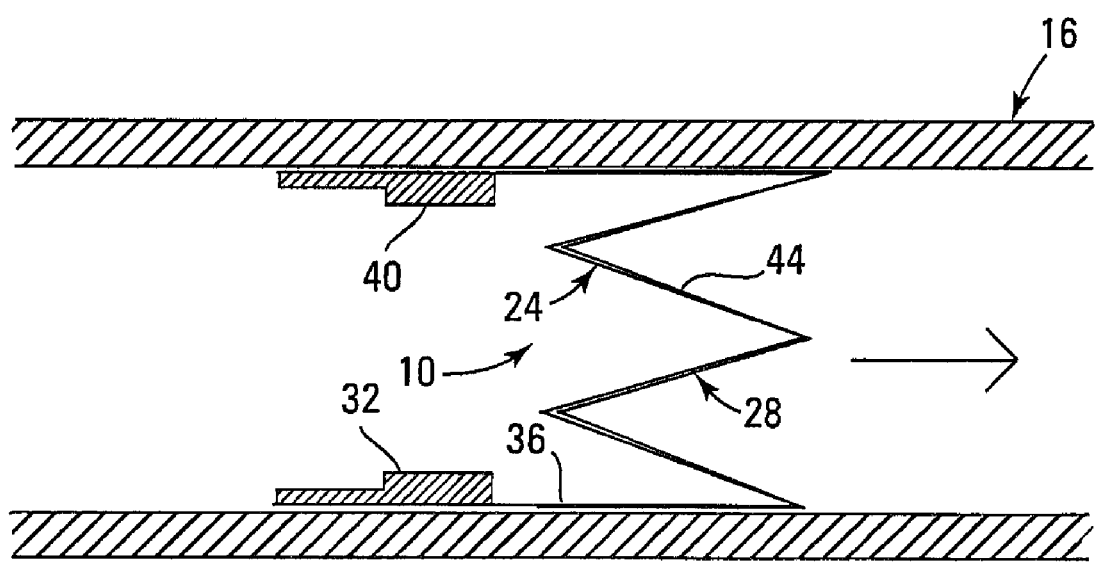
FIG. 2 is a close-up schematic view of a sensor module system deployed at a location within the pulmonary artery according to an embodiment of the present invention.

FIG. 1 is a schematic view and FIG. 2 is a close-up schematic view of a sensor system 10 implanted within a pulmonary artery 16 of a heart 20, according to one embodiment of the present invention. In other embodiments, the sensor system 10 may be implanted in a branch of the pulmonary artery 16 (e.g., the right or left pulmonary artery). In still other embodiments, the sensor system 10 may be implanted in other regions of the patient's vasculature or in other body lumens.

According to one embodiment of the present invention, as shown in FIG. 2, the sensor system 10 includes at least a first assembly 24 and a second assembly 28. Each assembly includes an implantable sensor module coupled to an anchor. According to the exemplary embodiment shown in FIG. 2, the first assembly includes a first sensor module 32 coupled to a first anchor 36. Similarly, the second assembly 28 includes a second sensor module 40 coupled to a second anchor 44.

The first assembly 24 is a pre-existing assembly delivered and deployed within the target vessel upon initiation of a treatment. Over time, the first assembly 24 may migrate away from the original target site or the sensor module 32 may fail to function properly or optimally due to one factor or another (e.g., battery failure, decreased sensing capacity, etc.) Rather than attempting to retrieve the existing first assembly 24, which can be made difficult by tissue ingrowth into the first assembly 24, the second assembly 28 can be delivered to the target site and deployed such that it at least partially overlies the first assembly 24. The first and second assemblies 24 and 28 are configured to overlap one another such that the second sensor module 40 is spaced apart from the first sensor module 32. Additionally, the assemblies overlie one another such that the first assembly 24 does not interfere with the functions or operations of the second assembly 28. According to a further embodiment of the present invention, the first and second assemblies 24 and 28 can be configured to further engage with additional assemblies (e.g., a third assembly, a fourth assembly, etc.).

FIG. 2 is a close-up schematic view of a sensor system 10 at a location within the pulmonary artery 16. As shown in FIG. 2, the second assembly 28 has been expanded against the pulmonary artery 16 from a location at least partially inside the first assembly 24, such that it at least partially overlies the first assembly 24. More specifically, the first anchor 36 of the first assembly 24 is at least partially engaged by the second anchor 44 of the second assembly 28. According to a further embodiment of the present invention, the second anchor 44 overlaps or overlies at least about half the length of the first anchor 36. Upon expansion against the inner wall of the pulmonary artery 16, the second anchor 44 functions to secure, anchor, or stabilize the first anchor 36. Partially overlapping the anchors 36 and 44 maximizes the overall anchor length, which may help further stabilize the system 10 within the pulmonary artery 16.

According to one embodiment of the present invention, the first sensor 32 and second sensor 40 are both disposed retrograde, with respect to the direction of blood flow in the vessel, from the anchors 36, 44. In the embodiment shown in FIG. 2, the sensors 32, 40 are each coupled to the anchors 36, 44 in a direction that is retrograde to the flow of blood through the pulmonary artery 16. Alternatively, the sensors 32, 40 can be each coupled to the anchors 36, 44 in a direction that is anterograde with the flow of blood through the pulmonary artery 16. According to one embodiment, the first anchor 36 overlaps the second anchor 44 such that the first sensor module 32 is circumferentially offset from the second sensor module 40. According to another exemplary embodiment of the present invention, the first sensor module 32 is offset within the artery/vessel at least 10 degrees from the second sensor module 40. According to another exemplary embodiment, the first sensor module 32 is circumferentially offset by about 90 degrees to about 180 degrees from the second sensor module 40.

Figure 3:
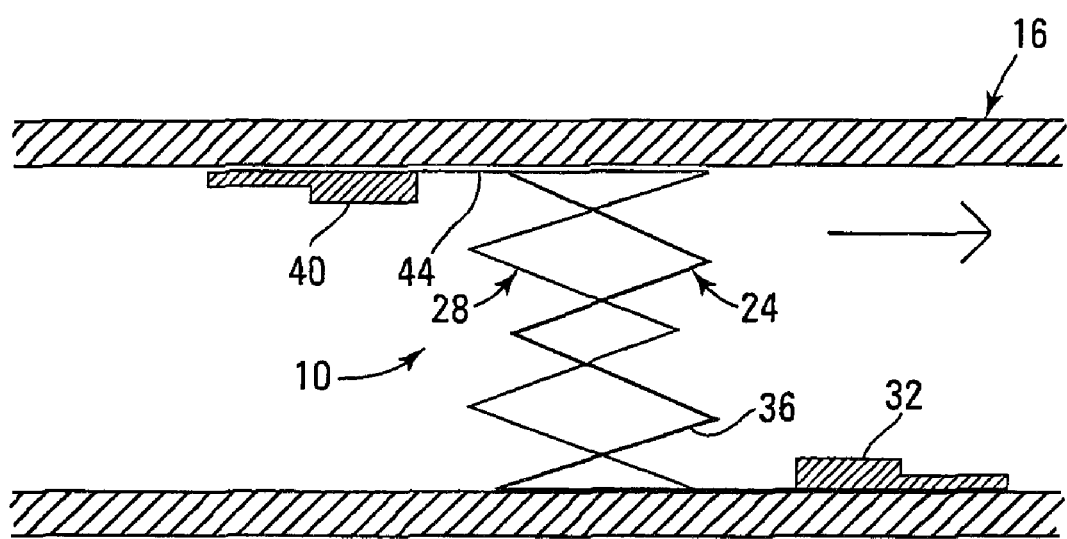
FIG. 3 is a close-up schematic view of a sensor module system deployed at a location within the pulmonary artery according to another embodiment of the present invention.

FIG. 3 is a close-up schematic view of the sensor system 10 deployed within the pulmonary artery 16 according to another embodiment of the present invention. As shown in FIG. 3, the sensors 32 and 40 are disposed in opposite direction with respect to the anchors 36 and 44. The first sensor 32 is coupled to the first anchor 36 such that it is orientated in a direction that is anterograde with the flow of blood in the pulmonary artery 16. The second sensor 40 is coupled to the second anchor 44 such that it is orientated in a direction that is retrograde to the flow of blood in the pulmonary artery 16. Additionally, the first anchor 36 overlaps the second anchor 44 such that the first sensor module 32 is longitudinally offset from the second sensor module 40. The sensor modules 32 and 40 may be longitudinally offset from one another along the same axis (i.e. 180 degrees). Alternatively, the sensor modules 32 and 40 may be longitudinally offset as well as circumferentially offset from one another as shown in FIG. 3.

Figure 4:
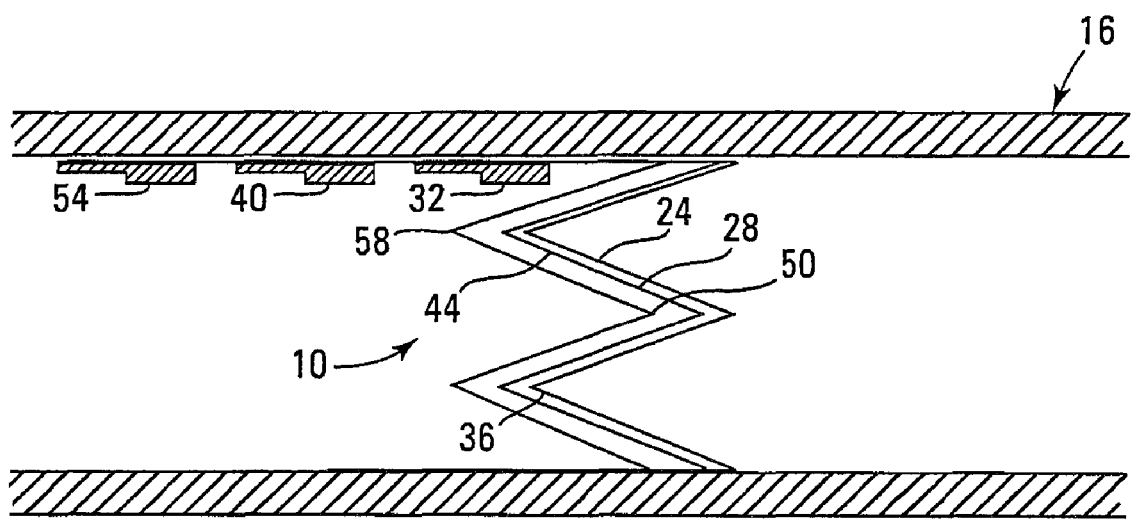
FIG. 4 is a close-up schematic view of a sensor module system deployed at a location within the pulmonary artery according to yet another embodiment of the present invention.

FIG. 4 is a close-up schematic view of a sensor system 10 according to yet another embodiment of the present invention. According to the embodiment shown in FIG. 4, three assemblies 24, 28, and 50 are shown in overlapping relationship with one another. Each assembly 24, 28, and 50 includes a sensor module 32, 40, and 54, coupled to an anchor 36, 44, and 58, respectively. The assemblies 24, 28 and 50 have been delivered to a location within the pulmonary artery 16 in a pre-determined order with each assembly 24, 28, and 50 being configured to at least partially overlie the next assembly. For each assembly 24, 28, and 50 the point at which the sensor module 32, 40 and/or 54 is coupled to the anchor 36, 44 and/or 58 differs in length with the first anchor 36 having the shortest length of attachment to its sensor module 36. The length increases with each subsequent assembly. Thus, sensor module 54 coupled to anchor 58 has the greatest length of attachment. This configuration permits the sensor modules 32, 40 and 54 to be spaced apart from one another when their anchors 36, 44, and 58 are partially or fully overlapped. As shown in FIG. 4, the sensor modules 32, 40 and 54 are offset from one another along a longitudinal axis of the anchor assemblies 24, 28, and 50. When the assemblies 24, 28 and 50 are overlapped, the length of the anchoring structure is maximized further stabilizing and securing the sensor module system 10 at a location within the pulmonary artery 16.

According to one exemplary embodiment of the present invention, the anchors 36, 44, and/or 58 have a stent-like configuration and are substantially cylindrical. Exemplary anchors are shown and described in U.S. Provisional Application Ser. No. 60/844,821, entitled "Anchor for an Implantable Sensor", which is herein incorporated by reference. The anchors 36, 44, and/or 58 are configured to transition between a collapsed configuration and an expanded configuration. In the collapsed configuration the anchors 36, 44, and/or 58 are configured to be delivered to a target site within the vessel of interest via a delivery catheter or other similar device. Upon deployment and expansion within the vessel, the anchors 36, 44, and/or 58 are adapted to engage the inner surface of the pulmonary artery and have an outer diameter that is slightly greater than the inner diameter of the vessel or artery in which they are deployed. When expanded, the anchors 36, 44, and/or 58 exert a radial expansion force against the arterial walls of the pulmonary artery or other vessel in which they are deployed, securing and stabilizing the assemblies within the artery at a desired location. Force is distributed along the expanded length of the anchors 36, 44, and/or 58 providing for a more effective and stable anchoring mechanism.

The stent-like anchors 36, 44, and/or 58 described above can be self-expanding or balloon expandable, and can be made from any materials, whether now known or later developed, suitable for use in cardiovascular stents or similar implantable devices. By way of example only, suitable materials include stainless steel and a wide variety of alloys and polymers. For self-expanding embodiments, the anchors 36, 44, and/or 58 are made at least partially from materials having desirable shape memory and/or superelastic properties. Exemplary materials exhibiting suitable shape memory and superelasticity include shape memory polymers and nickel-titanium shape memory alloys such as Nitinol. In some embodiments, the anchors 36, 44, and/or 58 are laser cut from a Nitinol tube.

The anchors 36, 44, and/or 58 need not be the same. For example, one anchor may be a self-expanding anchor, while the other anchor is a balloon-expandable anchor. Additionally the anchors 36, 44, and/or 58 may include rounded edges to prevent one anchor from entangling with another anchor and to minimize tissue damage at the deployment site. For all of the various embodiments of the present invention, the size of the stent-like anchors 36, 44, and/or 58, in both the collapsed and expanded configurations, will generally be determined based on the particular patient anatomy.

According to a further embodiment of the present invention, each anchor 36, 44, and/or 58 may include one or more alignment features that facilitate engagement of one anchor 36, 44, and/or 58 with another. According to one exemplary embodiment of the present invention, the alignment features are interlocking features that function to hold two or more anchors in an overlapping fashion such that their sensor modules are spaced at a distance from one another. In this embodiment the first anchor has a first alignment feature adapted to interlock with a second alignment feature located on the second anchor. One such exemplary interlocking feature is a bayonet-style locking feature. A bayonet-style locking feature may be located on each of the anchors. The bayonet-style locking features are configured to hook onto one another or alternatively, hook onto a portion of the stent-like anchoring structure. Under visualization (e.g., via fluoroscopy), the second assembly is guided to a location proximate to the location of the first assembly. The position of the first assembly including the first anchor is evaluated and the first alignment feature is located. The second assembly is then positioned and adjusted as necessary such that the second alignment feature will interlock with the first alignment feature. The interlocking features insure the position of the second assembly with respect to the first assembly such that the sensor modules are spaced apart from one another.

According to another embodiment of the present invention, at least one anchor 36, 44, and/or 58 may include one or more radiopaque markers to facilitate the overlapping of one anchor with one another. The radiopaque marker or markers can be used to guide the insertion of a second anchor within a first anchor. Once the second anchor is inserted within the first anchor the radiopaque marker or markers can be used to position the second anchor relative to the first anchor such that their sensor modules are spaced at a distance from one another and/or to prevent over extension of one anchor beyond another.

According to a further embodiment of the invention, at least one of the anchors 36, 44, or 58 may include a therapeutic coating. The therapeutic coating can include one or more therapeutic agents including, but not limited to, an antineoplastic agent, an antiproliferative agent, an anti-inflammatory agent, and antibiotic or combinations thereof. Additionally, the coating may be designed to allow the therapeutic agent to elute over a period of time.

As described above, each of the assemblies 24, 28 and 50 include a sensor module, 32, 40, and 54 coupled to anchors 36, 44, and 58, respectively. The sensor modules 32, 40, and/or 54 are configured to communicate with a pulse generator or other implantable device via a communication link, which may be wired or wireless. Various types of wireless communication circuitry are well-known in the art and the specific type and/or style of wireless communication that can be used with the system 10 is not limited. For example, ultrasonic waves, acoustic communications, radio frequency communications, and the like may be used. In one embodiment, the sensor modules 32, 40, and/or 54 include an acoustic transmitter/receiver configured for acoustic telemetry, which transmitter/receiver is configured to transmit and/or receive ultrasonic signals to/from a pulse generator or other implantable device. In some embodiments, the sensor modules 32, 40, and/or 54 may be configured to communicate with one or more other implantable medical devices (e.g., another pulse generator or other therapeutic device such as a drug delivery device) via other wired or wireless communication links. In still other embodiments, the sensor modules 32, 40, and/or 54 may be configured to communicate with devices external to the patient's body via wireless communication links.

The sensor modules 32, 40, and/or 54 may be configured to perform one or more designated functions, which may include taking one or more physiological measurements. The sensor modules 32, 40, and/or 54 may be configured to measure any known physiologic parameters such as, for example, blood pressure, temperature, blood or fluid flow, strain, electrical, chemical, or magnetic properties within the body. The specific parameters to be measured, and thus the implantation site for the first and subsequent assemblies 24, 28, and 50, are determined based on the particular therapeutic needs of the patient. In one exemplary embodiment, the sensor modules 32, 40, and/or 54 are configured to measure blood pressure in the pulmonary artery 16. In this embodiment, the sensor modules 32, 40, and/or 54 are configured to store and/or transmit blood pressure data to a pulse generator or other device e.g., a monitor or programmer) located external to the patient's body.

Figure 5:
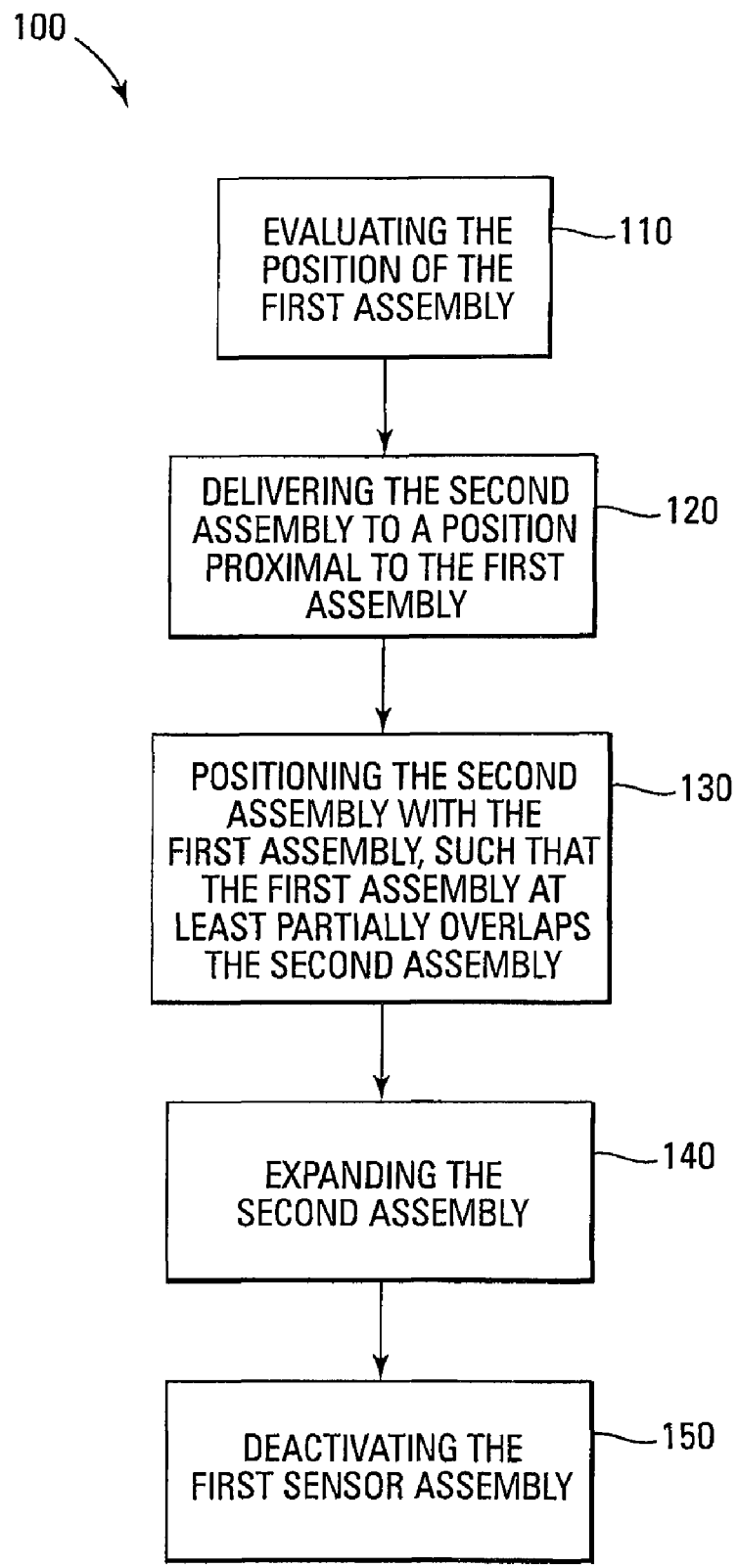
FIG. 5 is a block diagram of a method of overlapping a first assembly including a sensor module with a second assembly according to yet another embodiment of the present invention.

FIG. 5 is a block diagram showing a method 100 of overlapping a first assembly including a first sensor module coupled to a first anchor with a second assembly including a second sensor module coupled to a second anchor according to one embodiment of the present invention. The method 100 shown in FIG. 5 can also be applied to subsequent assemblies. As used herein, the term "overlap" means that the second or subsequent assembly is inserted within the first assembly such that the first anchor of the first assembly at least partially overlies the second anchor of the second assembly. The first and second assemblies 24 and 28 are configured to overlap one another such that the second sensor module 40 is spaced apart from the first sensor module 32. Additionally, the assemblies 24 and 28 overlap one another such that the first assembly 24 does not interfere with the functions or operations of the second assembly 28. According to a further embodiment of the present invention, the first and second assemblies 24 and 28 can be configured and delivered to a location within the pulmonary artery 16 in a pre-determined order such that they permit overlap with additional assemblies.

The first assembly 24 is a pre-existing assembly that is delivered to a location within the pulmonary artery 16 upon initiation of a treatment. Over time, the first sensor module 32 may fail due to any number of reasons. Thus, it may be desirable to replace the first sensor module 32 with a new functional sensor module at the same approximate location. Rather than retrieving the first anchor assembly 24, a second assembly 28 including a second sensor module 40 coupled to a second anchor 44 can be delivered within the first anchor assembly 24 so that the functions of the second sensor module 40 can replace the functions of the defunct first sensor module 32. In order to ensure accurate placement and overlap of the first assembly 24 with the second assembly 28, the position of the first assembly 24 within the pulmonary artery 16 is evaluated (block 110) using a fluoroscope or another suitable viewing device. A radiopaque marker on the first anchor 32 can aid in determining the position of the first assembly 24 within the pulmonary artery 16. Diagnostic testing (if applicable) of the first sensor module 32 can also be performed to determine the status of the sensor module.

Once the position of the first assembly 24 has been determined, a second assembly 28, including a second sensor module 40 coupled to a second anchor 44, is delivered under visualization to a position that is within the first assembly 24 such that the first anchor 36 of the first assembly 24 at least partially overlaps the second anchor 44 of the second assembly 28 (block 130). The second anchor 44 of the second assembly 28 is then expanded (block 140). If the anchor 28 is a self-expanding anchor, a delivery catheter or other tool is retracted allowing the anchor 44 to expand to a preformed shape having a pre-determined effective outer diameter. If the anchor 44 is a balloon-expandable anchor, a balloon is inflated to expand the anchor. If a balloon expandable anchor is selected, the balloon can be used to fine tune or adjust the position of the second anchor before expansion within the first anchor by first partially inflating the balloon to partially expand the anchor. Once a satisfactory position has been achieved, the second anchor 44 then can be fully expanded. In the event that the function of the second sensor module 40 is to replace the first sensor module 32, the first sensor module 32 is deactivated and the second sensor module 40 is activated (block 150).

Figure 6A:
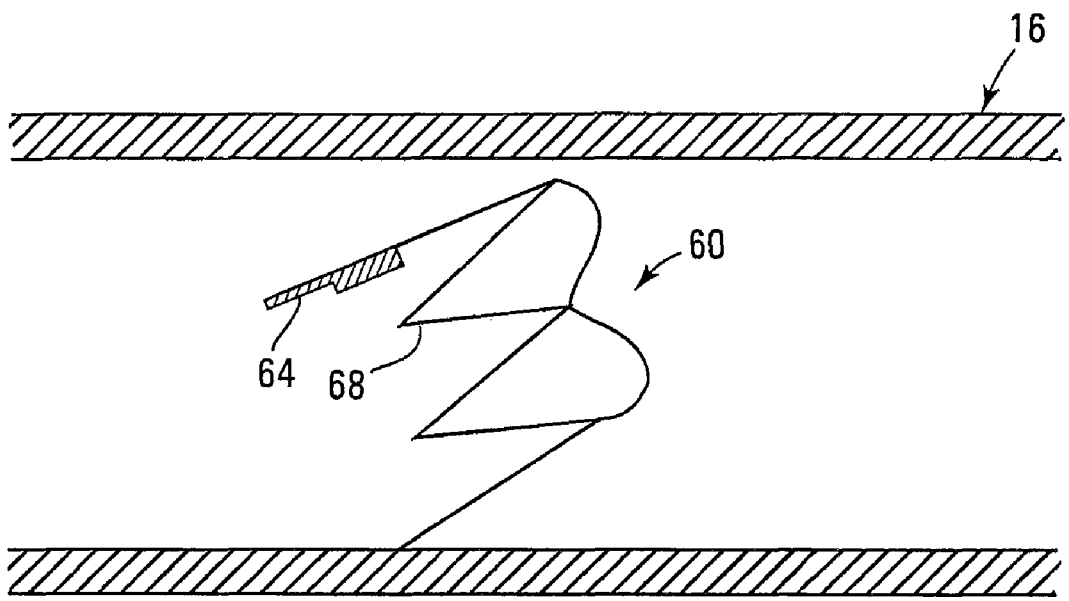
FIG. 6A is a close-up schematic view of a first assembly that has migrated away from its original position according to one embodiment of the present invention.
Figure 6B:
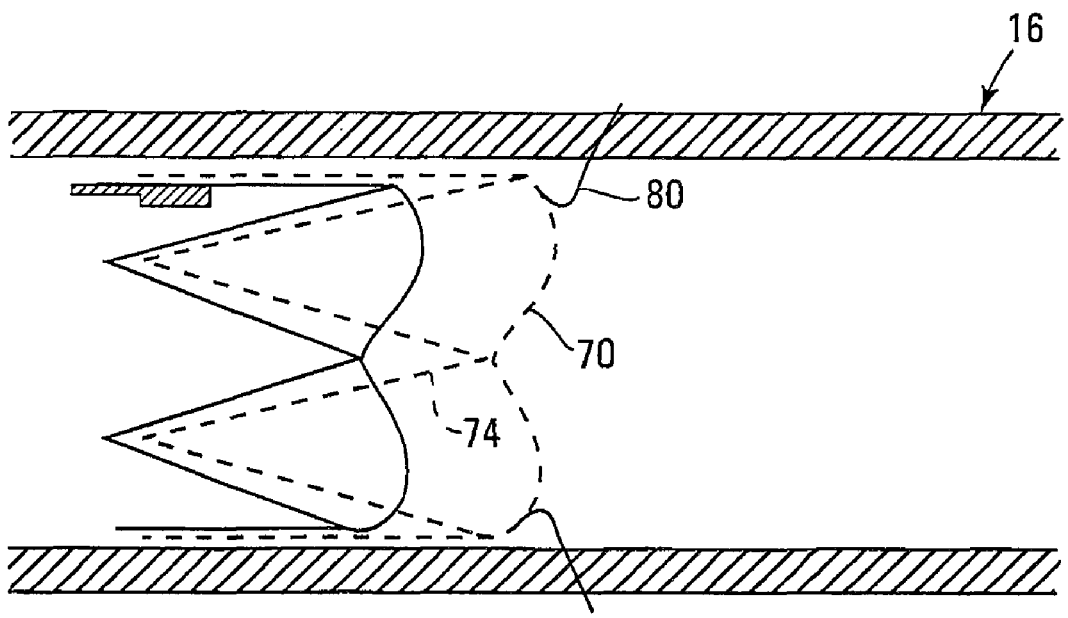
FIG. 6B is a close-up schematic view of a second assembly reinforcing the position of the first assembly shown in FIG. 5A according to one embodiment of the present invention.

According to another embodiment, shown in FIGS. 6A and 6B, the present invention is a method of reinforcing a first assembly at a location within the pulmonary artery. Anchors in the pulmonary artery are subjected to a variety of stresses particularly due to movements of the vessel. Additionally, the shape or inner diameter of the artery may change over time. As a result, the anchor can dislodge and migrate from the desired target location.

FIG. 6A shows an assembly 60 including a sensor module 64 coupled to an anchor 68 that has become dislodged from its original position within the pulmonary artery 16. Reinforcement of the existing assembly 60 is accomplished using a method similar to the one described above with reference to FIG. 5. In order to reinforce the position of the first anchor 68 and to stabilize the position of the existing assembly 60 within the pulmonary artery 16, a second assembly 70 is delivered to a location within the pulmonary artery 16. According to one exemplary embodiment, the second assembly 70 includes an expandable anchor 74. According to an alternative exemplary embodiment, the second assembly 74 also includes a second sensor module coupled to the expandable anchor 74. The expandable anchor 74 is configured to transition from a collapsed configuration to an expanded configuration. In the expanded configuration, the expandable anchor 74 expands such that it engages the inner surface of the pulmonary artery 16. According to one exemplary embodiment, the expandable anchor 74 expands to a diameter that is slightly larger than the inner diameter of the pulmonary artery 16.

The second assembly 70 is positioned within the first assembly 60 such that the first anchor 68 at least partially overlaps the anchor 74 of the second assembly 70. The second anchor 74 is then expanded, reinforcing and stabilizing the first assembly 60 within the pulmonary artery 16. If the second assembly 70 includes a sensor module the sensor module can be activated immediately or at a later time, as required.

According to yet a further embodiment of the present invention, the expandable anchor 74 of the second assembly 70 can include hooks 80 or other anchoring means that are adapted to engage the inner wall of the pulmonary artery 16 or other vessel in which the assemblies 60 and 70 are deployed. The hooks 80 provide for further reinforcement and stabilization of the original assembly 60 in the pulmonary artery 16.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of overlapping a first assembly including a first expandable anchor coupled to a first sensor module with a second assembly including a second expandable anchor coupled to a second sensor module within an artery or blood vessel, each of the first and second expandable anchors being configured for transition between a collapsed configuration and an expanded configuration, the method comprising:
   locating a position of the first assembly at a target location within the artery or blood vessel;
   delivering the second assembly with the second expandable anchor in its collapsed configuration to a position proximate the target location within the artery or blood vessel;
   positioning the second assembly within the first assembly such that the first expandable anchor at least partially overlaps the second expandable anchor; and
   expanding the second expandable anchor to its expanded configuration.

2. The method of claim 1, further comprising aligning a first alignment feature located on the first anchor with a second alignment feature located on the second anchor.

3. The method of claim 1, further comprising adjusting the position of the second sensor module assembly.

4. The method of claim 1, further comprising deactivating the first sensor module.

5. The method of claim 1, further comprising activating the second sensor module.

6. A method of overlapping a first assembly including an expandable first anchor coupled to a first sensor module with a second assembly including a second expandable anchor coupled to a second sensor module within an artery or blood vessel, each of the first and second expandable anchors being configured for transition between a collapsed configuration and an expanded configuration, the method comprising:

locating and evaluating functionality of the first sensor module, the expandable first anchor having been previously expanded to its expanded configuration within the artery or blood vessel;

delivering the second assembly with the second expandable anchor in its collapsed configuration to a location proximate the first assembly within the artery or blood vessel;

positioning the second assembly within the first assembly within the artery or blood vessel such that the first expandable anchor at least partially overlaps the second expandable anchor; and expanding the second expandable anchor to its expanded configuration.

7. The method of claim 6, further comprising aligning a first alignment feature located on the first anchor with a second alignment feature located on the second anchor.

8. The method of claim 6, further comprising adjusting the position of the second sensor module assembly.

9. The method of claim 6, further comprising deactivating the first sensor module.

10. The method of claim 6, further comprising activating the second sensor module.

* * * * *